(12) United States Patent
Norris

(10) Patent No.: US 6,381,479 B1
(45) Date of Patent: Apr. 30, 2002

(54) PULSE OXIMETER WITH IMPROVED DC AND LOW FREQUENCY REJECTION

(75) Inventor: Mark A. Norris, Boulder, CO (US)

(73) Assignee: Date-Ohmeda, Inc., Madison, WI (US)

(*) Notice: Subject to any disclaimer, the term of this patent is extended or adjusted under 35 U.S.C. 154(b) by 0 days.

(21) Appl. No.: 09/466,316

(22) Filed: Dec. 17, 1999

(51) Int. Cl.$^7$ ............................................. A61B 5/00
(52) U.S. Cl. ..................................... 600/336; 600/322
(58) Field of Search .............................. 600/310, 322, 600/323, 330, 336; 330/75, 96

(56) References Cited

U.S. PATENT DOCUMENTS

| | | | |
|---|---|---|---|
| 4,065,726 A | * 12/1977 | Senger | 330/75 |
| 4,714,341 A | * 12/1987 | Hamaguri et al. | 600/310 |
| 4,781,195 A | 11/1988 | Martin | |
| 5,057,682 A | 10/1991 | Michon et al. | 250/214 |
| 5,094,239 A | * 3/1992 | Jaeb et al. | 600/330 |
| 5,111,817 A | * 5/1992 | Clark et al. | 600/323 |
| 5,490,505 A | * 2/1996 | Diab et al. | 600/323 |
| 5,539,354 A | 7/1996 | Carsten | 327/559 |
| 5,577,500 A | 11/1996 | Potratz | |
| 5,656,806 A | 8/1997 | Dautriche | 250/214 |
| 5,891,022 A | 4/1999 | Pologe | 600/323 |
| 5,954,644 A | 9/1999 | Dettling et al. | 600/322 |

* cited by examiner

Primary Examiner—Eric F. Winakur
(74) Attorney, Agent, or Firm—Marsh Fischmann & Breyfogle LLP

(57) ABSTRACT

A system for providing an improved DC and low frequency signal rejection in a photoplethysmographic measurement instrument is disclosed. The system is used in a measurement instrument which includes at least two signal sources (106, 108) for transmitting light signals at least at two wavelengths through a tissue of a test subject and a detector (112) for converting light signals transmitted through the tissue into a detector output signal. The system includes a DC restoration (114) which removes DC and low frequency signal components from the detector output signal prior to amplification thereof so as to avoid saturating amplified output signal with the low frequency signal component. The DC restoration (114) is configured to continuously remove low frequency signal component from the detector signal during dark intervals when the signal sources are deactivated, as well as during light intervals when one of the signal sources is activated. In one embodiment, the DC restoration is embodied in the form of a DC restoration circuit (200) which comprises a transimpedance amplifier (204, 206) which receives the detector output signal and produces an amplifier output signal (222) and an integrator feedback loop (208–220) which receives the amplified output signal and produces a bias current, wherein the bias current is used to subtract DC and low frequency signal components from the detector output signal prior to amplification of the detector signal by the amplifier.

17 Claims, 2 Drawing Sheets

PULSE OXIMETER WITH IMPROVED DC AND LOW FREQUENCY REJECTION

FIELD OF THE INVENTION

The present invention generally relates to photoplethysmographic measurement systems and, in particular, to a method and system which provides improved DC and low frequency rejection in a detector output signal prior to amplification thereof.

BACKGROUND OF THE INVENTION

In the field of photoplethysmography, light pulses from different portions of the electromagnetic spectrum are used to noninvasively determine various blood analyte related values in test subjects. Typically, photoplethysmographic measurement systems, such as pulse oximeters, include a probe for releasably attaching to the tip of a patient's appendage (e.g., finger, earlobe or nasal septum). The probe directs light signals (e.g., red and infrared signals) generated by first and second light sources into the appendage where the probe is attached. Some portions of the light signals are absorbed by the tissue, and the remaining portions of the light signals pass through patient tissue. The intensity of light passing through the tissue is monitored by a photodetector which produces intensity related signals indicative of light absorbency characteristics of the tissue. Because blood analytes to be identified within the patient's tissue absorb more light at one wavelength than at another wavelength, the intensity of light signals produced by the photodetector may be used to compute an amount of blood analyte (e.g., oxygen saturation of hemoglobin in arterial blood) present in the blood.

Ideally, the intensity related signals produced by the photodetector will accurately represent the amount of light absorbed by the tissue at different wavelengths. However, the intensity related signals, which typically include AC, DC and low frequency signal components, may be distorted by various factors. For example, the DC and low frequency signal components present in the intensity related signal can be photonic energy emitted by the light sources in the "off" state when the light sources are both deactivated. The DC and low frequency signal components may also be attributable to other factors such as, for example, ambient light sensed by the photodetector.

Generally, the high frequency AC portions of the detector signals contain the information that is necessary for calculating the blood analyte related values whereas, the DC and low frequency portion of the detector signal may constitute noise or interfere with processing of the detector signal information. For example, because the DC and low frequency portion of the detector signal is typically much larger than the AC portion, accurate representation of the AC portion of the detector signal may be lost during analog-to-digital conversion. Moreover, the DC and low frequency portion contained in the detector signal may prevent sufficient amplification thereof without saturating the detector signal with undesired DC and low frequency signal component.

Some instrument designs have attempted to address problems associated with such DC and low frequency signal components through the use of a capacitor or filter to separate such components from the AC component of interest. However, such approaches have generally had limited ability to remove low frequency and DC components from the detector signals before amplification, thereby possibly saturating the detector signals with undesirable signal components (e.g., ambient light, or photonic energy emitted in the "off" state) if the gain of the amplifier is set too high.

One other instrument design, disclosed in U.S. Pat. No. 4,781,195, attempts to address problems associated with such DC signal components by reducing or eliminating a dark current signal produced by a detector during "dark" intervals when light sources are disabled. This instrument design employs a switch coupled to a timing device to interrupt, during a selected portion of the signal cycle, the flow of electricity from a front end amplifier to a feedback loop that provides dark current correction. However, this switch incorporated into the instrument may reduce the effectiveness of the feedback loop, and the incorporation of the switch limits the amount of gain that can be achieved without saturation.

SUMMARY OF THE INVENTION

Thus, there is a need for a photoplethysmographic measurement system which improves the quality of an analog output signal produced by a detector. In particular, there is a need for a system that is capable of removing undesirable signal components (e.g., DC and low frequency signal components) from the detector signal, over a signal waveform cycle, before amplification such that the fall signal cycle can be amplified as desired without saturation.

The present invention is directed to a system and corresponding method for use in a pulse oximeter to improve the way in which DC and low frequency signal components (e.g., photonic energy emitted by the sources in the "off" state and/or ambient light) are removed from analog signals produced by a detector. According to the present invention, DC and low frequency signal components are continuously removed from the detector signals during the "dark" intervals when light sources are deactivated and also during "light" intervals when one of the light sources is activated. Because the DC and low frequency components are continuously canceled from the detector signals prior to amplification thereof, the gain of the amplifier may be increased without saturating the detector signal with undesirable signal components (e.g., noise including ambient light).

In accordance with one aspect of the present invention, photonic energy emitted by the light sources in the "off" state and noise (e.g., ambient light) are removed from the detector signals before being amplified. It has been recognized that the light sources may transmit as much as half and sometimes more than half of their photonic power in the "off" state. A desirable amount of gain may not be achieved without saturating the detector signals with undesirable signal components if such photonic energy and ambient light are not accounted for prior to amplification of the dectector signal. Because this photonic energy and ambient light are emitted in the form of DC and low frequency signals, the removal thereof from the detector output signals may be accomplished in accordance with the present invention by stripping DC and low frequency signal components from the detector signal over a full cycle of the signal.

In accordance with another aspect of the present invention, a DC restoration circuit is utilized to remove DC and low frequency signal components from the analog signals produced by the detector. The DC restoration circuit includes an amplifier for amplifying the output signals produced by the detector, which may be in the form of an electrical current signal. The DC restoration circuit preferably includes an integrator feedback stage connected to the amplifier to provide an integrator feedback current signal (i.e., opposite in sign to the detector current signal) to cancel undesirable signal components (e.g., DC and low frequency signal components) in the current signals produced by the detector at the input of the amplifier. Because the feedback stage is used to subtract DC and low frequency signal components from the detector signal at the input of the amplifier, a relatively high amplification gain can be achieved without saturating the amplified detector signal with undesirable signal components.

An electrical component (e.g., resistor), may be coupled to the integrator to selectively reduce the gain of the integrator. According to the present invention, any suitable type of integrator capable of providing a high gain at DC and low frequency may be employed. It should be appreciated that the integrator can be specifically configured to define the low frequency "roll-off" point of the integrator at any desirable frequency level selected to optimize the filtering of the undesirable (low frequency) signal components.

In accordance with a further aspect of the present invention, the configuration of the DC restoration circuit allows for incorporation thereof into pulse oximeters employing a variety of signal multiplexing mechanisms, e.g., including both time multiplexed and non-time multiplexed oximeters. Because the DC restoration circuit of the present invention functions independently of a demultiplexer or a timing device (e.g., light source driver), amplified output signals produced by the DC restoration circuit may be processed by any suitable demultiplexer (e.g., time or frequency division demultiplexer) to analyze the amplified output signal with respect to different wavelengths of light. In one embodiment, the separation of the amplified output signal into different wavelengths is accomplished by a software application running in a processor.

In accordance with yet another aspect of the present invention, a fixed voltage (e.g., zero volts) is maintained across the detector by the amplifier at all times. Because the integrator feedback current signal produced by the integrator feedback stage offsets the DC detector current to maintain a fixed voltage across the detector, a relatively wide range of amplification gain can be achieved without saturating the amplified signal with undesirable DC detector current.

DETAILED DESCRIPTION

Figure 1:
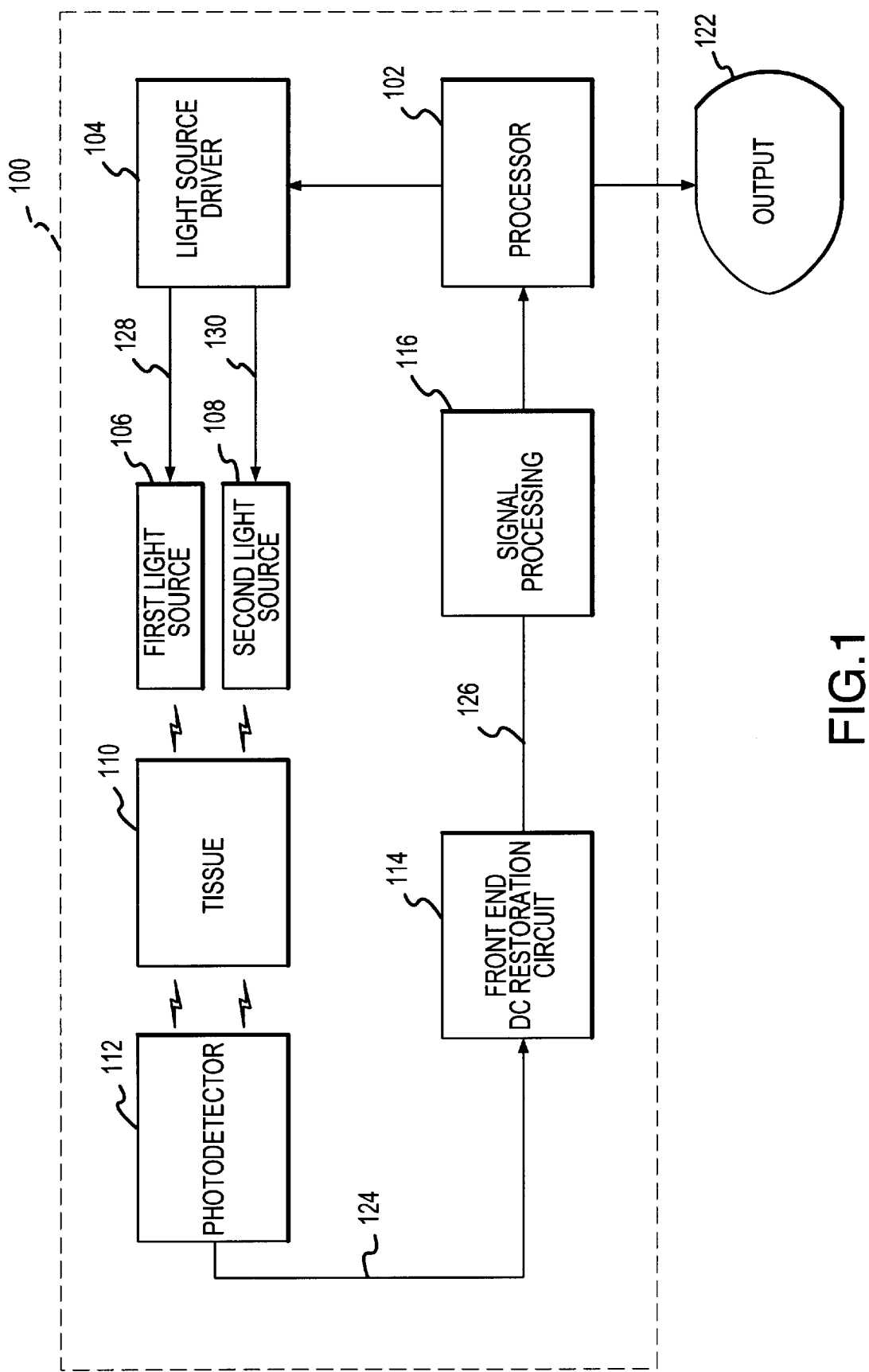
FIG. 1 is a block diagram illustrating a system which provides improved DC and low frequency signal component rejection using DC restoration in accordance with the present invention.

Referring to FIG. 1, a photoplethysmographic measurement system 100 for providing improved DC and low frequency signal rejection in accordance with the present invention is shown. According to the present invention, a front end DC restoration module 114 is used in a photoplethysmographic measurement instrument to address the problem of DC and low frequency components present in detector output signals 124 which components can be due to, for example, photonic energy emitted by light sources 106, 108 in the "off" state or ambient light. For ease of description, the measurement instrument will be described in terms of a pulse oximeter which noninvasively measures blood analyte related values.

Included in the pulse oximeter are at least two light sources 106, 108 which emit light signals at different predetermined wavelengths. In the illustrated pulse oximeter, two light sources (e.g., light emitting diodes (LEDs) or laser diodes) are utilized, one source for radiating light of the first wavelength (e.g., red light) and the other source for radiating light of the second wavelength (e.g., infrared light). The light sources are controlled by a light source driver 104 which generates drive signals 128, 130 to control the activation and deactivation of each light source. The light source driver 104 is controlled by the processor 102 to alternately emit light of the first and second wavelengths at regular intervals from the first and second light sources, respectively. According to the present invention, the DC restoration module 114 can be incorporated into a pulse oximeter which is configured to turn the light sources "on" and "off" in a non-alternating manner, e.g., frequency multiplexed or other multiplexed signals.

The pulse oximeter further includes a photodetector 112 which converts an incident light signal into a detector output signal 124. The incident light signal may include light from the sources 106 and 108 and ambient light. The detector signal 124 may be transmitted in the form of an electrical current signal. The DC restoration module 114 receives detector output signals 124 produced by the photodetector 112 and removes DC and low frequency signals therefrom prior to detector signal amplification. The signals 126 output by the DC restoration module 114 are transmitted to a processor 102 via signal processing circuitry 116.

The output signals 126 are transmitted to a processor 102 via signal processing circuitry 116. The signal processing circuitry 116 may include a digital to analog convertor and other electronics. For example, in certain implementations, the output signals may be split by a demultiplexer into wavelength channels prior to the processor 102. In such cases separate A/D convertors and other components may be provided for each channel. Alternatively, a software module may be provided in conjunction with the processor 102 for extracting the wavelength components from the composite signal.

Figure 2:
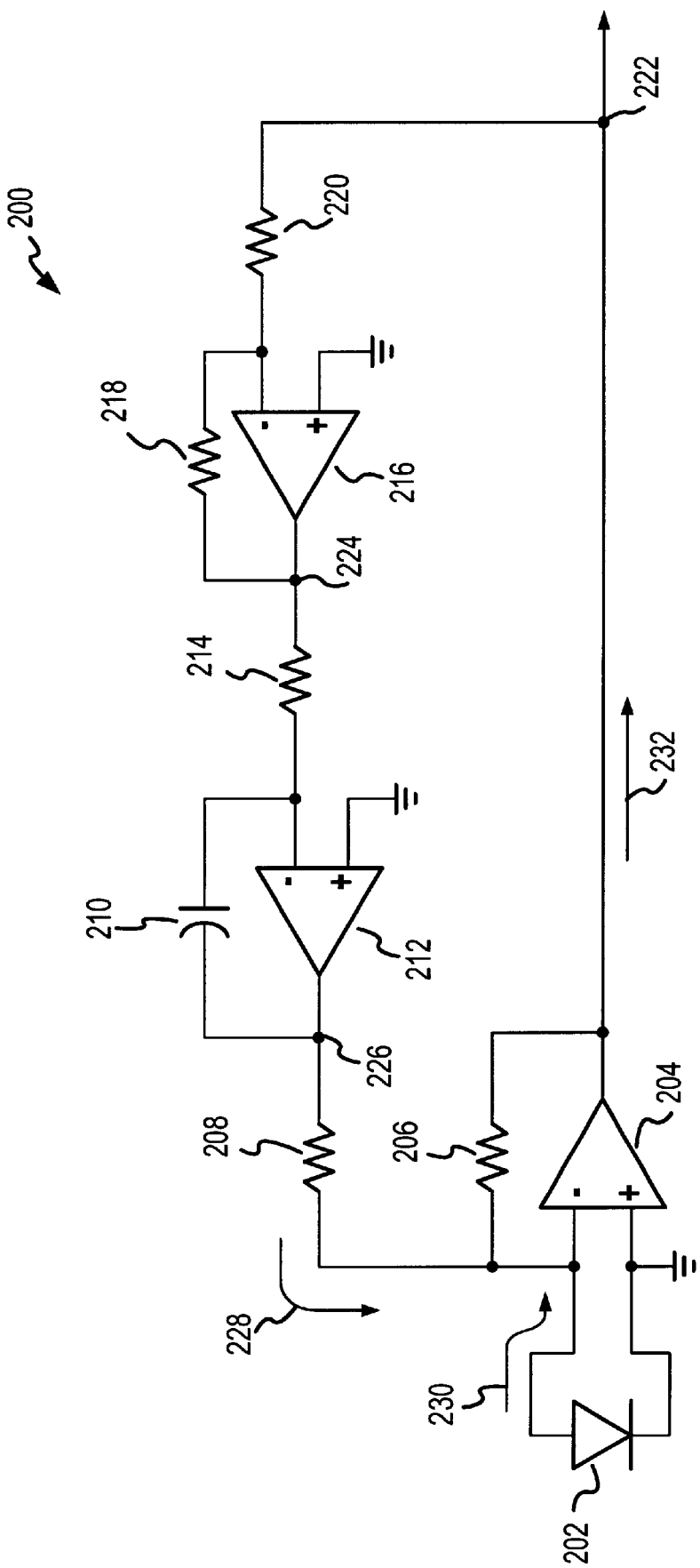
FIG. 2 is a circuit diagram illustrating a DC restoration module of the present invention with a photodetector shown in dotted lines.

Referring to FIG. 2, one embodiment of a DC restoration circuit 200 for use in a pulse oximeter is shown. For example, the illustrated circuit may be incorporated into DC restoration module 114 (FIG. 1). The illustrated DC restoration circuit 200 includes a transimpedance amplifier (204, 206) and an integrator feedback loop (208–220). The current signal 230 produced by a photodetector 202 is received by the transimpedance amplifier (204,206) which converts the current signal 230 received into a voltage signal 232. The integrator feedback loop is connected to receive the voltage signal produced by the transimpedance amplifier (204,206) to provide an integrator feedback current signal 228, which is opposite in sign to the detector current signal 230, to cancel undesirable signal components (e.g., DC and low frequency signal components) in the detector current signal at the input of the transimpedance amplifier. The illustrated transimpedance amplifier includes an operational amplifier 204 and a feedback resistor 206. The feedback resistor 206 of the transimpedance amplifier can be a variable resistor to allow a user to select an impedance of the resistor to achieve an optimal gain.

As noted above, the output of the transimpedance amplifier is connected to an integrator feedback loop which includes an inverter, an integrator and a resistor 208. The inverter includes an operational amplifier 216 with a feedback resistor 218 coupled to the inverting input thereof and an input resistor 220 connecting the output of the transimpedance amplifier to the inverting input of the inverter amplifier 216. The inverter is connected to an integrator which serves to amplify DC and low frequency signals transmitted thereby. Theoretically, the AC voltage gain of an integrator should vary inversely with frequency (e.g., a very high gain at low frequency and ideally infinite at DC). However, integrators have a finite open loop gain which causes integration to cease at some low frequency. It should be appreciated that the integrator may be configured to define the low frequency "roll-off" point of the integrator at a desirable frequency level. It should be further appreciated that the illustrated integrator may be modified or replaced with other types of integrators that are capable of providing a high gain at DC and low frequency.

The illustrated integrator includes an operational amplifier 212 with a feedback capacitor 210 coupled to the inverting input thereof and an input resistor 214 connecting the output of the inverter amplifier to the inverting input of the integrator amplifier. The output of the integrator is connected to the transimpedance amplifier via the voltage to current resistor 208 which serves to selectively reduce the gain of the integrator. The integrated feedback current signal 228 generated by the integrator is presented to the input of the transimpedance amplifier to subtract low frequency and DC component from the incoming detector current 230.

In accordance with the present invention, because the integrated feedback current signal 228 is presented to the input of the amplifier 204 not only during the "dark" intervals when the light sources are deactivated but also during "light" intervals when one of the light sources is activated, this subtraction process maintains the voltage across the detector 202 at a fixed voltage (e.g., zero) at all times. Moreover, the DC restoration circuit of the present invention is configured to continuously remove DC and low frequency components (e.g., photonic energy and ambient light) from the detector signals during the "dark" intervals as well as during the "light" intervals. In this regard, a relatively high gain can be achieved by the transimpedance amplifier without saturating the amplified signal with the undesirable signal components.

In addition and as noted above, the DC restoration circuit 200 described herein can be incorporated into a pulse oximeter employing any light source driving configuration. Furthermore, because the DC restoration of the present invention performs independently of a demultiplexer or a timing device, the DC restoration circuit 200 can be incorporated into a pulse oximeter utilizing any suitable demultiplexer, including a time division demultiplexer and a frequency division demultiplexer. In one embodiment, the separation of detector output signals into different wavelengths is accomplished by a software application running in a processor.

The operation of the present system will be described by first referring to FIG. 1. The light pulses generated by the light sources 106, 108 are transmitted through a tissue 110 of a test subject and strike the photodetector 112 which creates electrical current signal 124 in response thereto. The magnitude of the detector current signal 124 is proportional to the power of light striking the photodetector. Referring now to FIG. 2, the transimpedance amplifier (204,206) converts the current signal 230 received from the photodetector 202 into a voltage signal 232 which has an electrical polarity opposite to the detector current signal. The voltage signal 232 output by the transimpedance amplifier is received at the input of the inverter which reverses the polarity of the voltage signal and presents an inverter voltage signal at 224, which has the same electrical polarity as the detector current signal, to the integrator. The integrator serves to amplify DC and low frequency signals contained in the inverter voltage signal and outputs an integrator voltage signal at 226. The voltage signal output by the integrator is converted to a current signal by the resistor 208. The current signal 228 output by the resistor 208, having an opposite electrical polarity as the detector current signal, is fed back to the input of the transimpedance amplifier. In this regard, the integrator feed back loop, consisting of the integrator, inverter and resistor, serve to cancel DC and low frequency signal components from the detector current signal before amplification thereof.

Referring back to FIG. 1, the amplified signal 126 produced by the DC restoration circuit 114 is transmitted to the processor 102 The processor 102 separates first and second portions (e.g., red and infrared signals) of the amplified signal corresponding to the light signals produced by the first and second light sources 106, 108 (e.g., red and infrared light emitting diodes) and converts the separated analog portions into digital data before performing blood analyte computations. Because the DC and low frequency signal components are rejected by the DC restoration circuit prior to amplification, the remaining AC portion of the detector signals can be sufficiently amplified by the DC restoration circuit 114 before being digitized by the processor 102 so that accurate representation of the AC portion is preserved during analog-to-digital conversion. In this way, the DC restoration circuit improves the quality of analog signals produced by the detector to more accurately represent the amount of light signals absorbed by the tissue at different wavelengths by amplifying AC portions of the analog signals before digitization thereof. Finally, the analog and digital processor 102 computes blood analyte related values (e.g., oxygen saturation levels) by processing the digitized data which is indicative of light absorbency characteristics of the tissue 110.

Alternative embodiments of the DC restoration circuitry are possible. The integrator (210–214) may be replaced with a non-inverting amplifier configuration, with a passive RC network to continue rolling off the response of the integrator after the non-inverting amplifier goes to unity gain. The voltage to current resistor 208 may be replaced with an active current source. Such a configuration permits increased bandwidth in a transimpedance amplifier (204, 206) with a bandwidth limited operational amplifier 204.

While the foregoing preferred embodiments of the invention have been described and shown, it is understood that variations and modifications, such as those suggested and others within the spirit and scope of the invention, may occur to those skilled in the art to which the invention pertains. Accordingly, the scope of the present invention is to be defined as set forth in the appended claims.

What is claimed is:

1. An apparatus for use in a measurement instrument which includes at least two signal sources which generate a light signal at least at two wavelengths and transmit said light signal through a tissue of a test subject and a detector which receives said light signal transmitted through the tissue and converts said light signal received into a detector signal, said apparatus comprising:

means for receiving said detector signal;

means for removing DC and low frequency signal components below a defined frequency from said detector signal received by employing a feedback signal based on said detector signal to cancel, at least in part, said DC and low frequency signal components, so as to generate a filtered output signal; and means for amplifying said filtered output signal to generate an amplified output signal;

wherein a blood analyte related value in the tissue of the test subject is computed based on said amplified output signal.

2. The apparatus of claim 1, wherein said removing means continuously removes said DC and low frequency signal components from said detector signal during dark intervals when said signal sources are deactivated and during light intervals when at least one of said signal sources is activated.

3. The apparatus of claim 1, comprising wherein said removing means comprises a DC restoration circuit including an amplifier for amplifying a DC or low frequency signal component so as to provide said feedback signal.

4. The apparatus of claim 3, wherein said DC restoration circuit comprises:

at least one amplifier which receives said detector signal and produces an amplifier output signal;

an integrator feedback loop which receives said amplifier output signal and produces a bias current; and wherein said bias current is used to subtract DC and low frequency signal components from said detector signal prior to amplification of said detector signal by said amplifier.

5. The apparatus of claim 4, wherein said integrator feedback loop comprises:

at least one integrator which receives said amplifier output signal and amplifies DC and low frequency signal components contained in said amplifier output signal to produce a bias voltage; and at least one resistor which receives said bias voltage and produces said bias current to be supplied to said amplifier, wherein said resistor serves to reduce the gain of said integrator.

6. A pulse oximeter for noninvasively measuring a blood analyte related value in a tissue of a test subject, comprising:

at least two signal sources which generate a light signal at least at two wavelengths and transmit said light signal through the tissue;

a detector which receives said light signal transmitted through the tissue and converts said light signal received into a detector signal;

a DC restoration which removes DC and low frequency signal components below a defined frequency from said detector signal by employing a feedback signal based on said detector signal to cancel, at least in part, said DC and low frequency signal components, so as to generate a filtered output signal and amplifies said filtered output signal to generate an amplifies output signal; and a processor which receives said amplified output signal and computes a blood analyte related value in the tissue of the test subject based on said amplified output signal received.

7. The pulse oximeter of claim 6, wherein said DC restoration continuously removes said DC and low frequency signal components from said detector signal during dark intervals when said signal sources are deactivated and during light intervals when at least one of said signal sources is activated.

8. The pulse oximeter of claim 6, further comprising a demultiplexer for separating said amplified output signal into at least two different wavelengths of light prior to computation of said blood analyte related value.

9. The pulse oximeter of claim 8, wherein said demultiplexer is selected from one of the following: a frequency division demultiplexer and a time division demultiplexer.

10. The pulse oximeter of claim 6, wherein said DC restoration circuit comprises:

a transimpedance amplifier which receives said detector signal and produces a transimpedance amplifier output signal;

an integrator feedback loop which receives said transimpedance amplifier output signal and produces a bias voltage; and a voltage to current resistor which receives said bias voltage and produces a bias current to be supplied to said transimpedance amplifier;

wherein said bias current is used to subtract DC and low frequency signal components from said detector output signal prior to amplification of said detector output signal by said transimpedance amplifier.

11. The pulse oximeter of claim 10, wherein said integrator feedback loop comprises:

at least one integrator which receives said amplifier output signal and amplifies DC and low frequency signal components contained in said amplifier output signal to produce a bias voltage; and at least one resistor which receives said bias voltage and produces said bias current to be supplied to said amplifier, wherein said resistor serves to reduce the gain of said integrator.

12. A method for use in a measurement instrument which includes at least two signal sources which generate light signal at least at two wavelengths and transmit said light signal through a tissue of a test subject and a detector which receives said light signal transmitted through the tissue and converts said light signal received into a detector signal, said method comprising the steps of:

receiving said detector signal;

removing DC and low frequency signal components below a defined frequency from said of said detector signal by employing a feedback signal based on said detector signal to cancel, at least in part, said DC and low frequency signal components, so as to generate a filtered output signal;

amplifying said filtered output signal to generate an amplified output signal;

computing a blood analyte value in the tissue of the test subject based on said amplified output signal.

13. The method of claim 12, wherein said removing step is configured to continuously remove said DC and low frequency signal components from said detector signal during dark intervals when said signal sources are deactivated and during light intervals when at least one of said signal sources is activated.

14. The method of claim 12, further comprising the step of separating said amplified output signal into at least two different wavelengths of light prior to computation of said blood analyte related value.

15. The method of claim 14, wherein said step of separating said amplified output signal is accomplished with one of the following: a frequency division demultiplexer and a time division demultiplexer.

16. The method of claim 12, wherein said step of removing DC and low frequency signal components further comprises the step of producing a bias current to subtract DC and low frequency signal components from the detector signal before amplification thereof.

17. The method of claim 16, wherein said step of producing a bias current is accomplished with an integrator feedback loop which comprises:

at least one integrator which receives said amplifier output signal and amplifies DC and low frequency signal components contained in said amplifier output signal to produce a bias voltage; and at least one resistor which receives said bias voltage and produces said bias current, wherein said resistor serves to reduce the gain of said integrator.

* * * * *

UNITED STATES PATENT AND TRADEMARK OFFICE
CERTIFICATE OF CORRECTION

PATENT NO.     : 6,381,479 B1
DATED          : April 30, 2002
INVENTOR(S)    : Norris It is certified that error appears in the above-identified patent and that said Letters Patent is hereby corrected as shown below:

<u>Title page,</u>
Item [73], delete "Date-Ohmeda, Inc.", and insert therefor -- Datex-Ohmeda, Inc. --;

<u>Column 7,</u>
Line 42, delete "amplifies", and insert therefor -- amplified --.

Signed and Sealed this

Sixteenth Day of July, 2002

Attest:

JAMES E. ROGAN
Attesting Officer    Director of the United States Patent and Trademark Office